United States Patent [19]
Herold

[11] Patent Number: 4,645,856

[45] Date of Patent: Feb. 24, 1987

[54] PROCESS FOR THE PREPARATION OF PERDEUTERATED METHACRYLATES

[75] Inventor: Thomas Herold, Brensbach, Fed. Rep. of Germany

[73] Assignee: Merck Patent Gesellschaft mit beschrankter Haftung, Darmstadt, Fed. Rep. of Germany

[21] Appl. No.: 723,116

[22] Filed: Apr. 15, 1985

[30] Foreign Application Priority Data

Apr. 14, 1984 [DE] Fed. Rep. of Germany ....... 3414150

[51] Int. Cl.$^4$ .............................................. C07C 67/00
[52] U.S. Cl. .................................... 560/215; 556/417; 526/329.7; 428/394; 350/96.34; 560/205
[58] Field of Search ................. 556/417; 560/215, 205

[56] References Cited

U.S. PATENT DOCUMENTS

| | | | |
|---|---|---|---|
| 3,419,601 | 12/1968 | Isbell, Jr. | 560/215 |
| 3,466,320 | 9/1969 | Hargis | 560/215 |
| 4,138,194 | 2/1979 | Beasley et al. | 428/394 X |
| 4,529,816 | 7/1985 | DeColibus et al. | 560/215 X |

OTHER PUBLICATIONS

Fieser, et al., Reagents for Organic Synthesis, vol. 10, (1982), p. 3, John Wiley & Sons, N.Y.

*Primary Examiner*—Joseph Paul Brust
*Attorney, Agent, or Firm*—Millen & White

[57] ABSTRACT

Perdeuterated methacrylates of a high degree of deuteration can be obtained by a process for the preparation of perdeuterated methacrylates from hexadeuteroacetone by conversion into the corresponding cyanohydrin, subsequent elimination of water, hydrolysis of the cyano group and esterification with perdeuterated alkanols, the conversion of hexadeuteroacetone into the cyanohydrin being effected by reaction with trimethylsilyl cyanide to give 1,3-hexadeutero-2-(trimethylsiloxy)-2-cyano-propane and subsequent hydrolytic elimination of the trimethylsilyl group.

2 Claims, No Drawings

PROCESS FOR THE PREPARATION OF PERDEUTERATED METHACRYLATES

BACKGROUND OF THE INVENTION

The invention relates to a novel process for the preparation of perdeuterated methacrylates with a high degree of deuteration.

In the preparation of optical fibres, materials based on organic polymers are gaining increasing importance, in addition to the inorganic glass materials. Polymethacrylates, in particular polymethyl methacrylate (PMMA), have proved to be very suitable due to their optical properties and material properties. It was found, however, that fibres based on PMMA still have light attenuation values which are too high for present-day requirements. Thus, for optical fibres of this material, these values are in the region of about 300 dB/km at a light wavelength of 650 nm. It has recently been found (Appl. Phys. Lett. 41, 802 (1982), and 42, 567 (1983)) that these attenuation values can be drastically reduced if the corresponding deuterated polymer is used in place of PMMA for the preparation of the fibres. Thus, with optical fibres of perdeuterated polymethyl methacrylate, which is accessible by polymerisation of deuterated methyl methacrylate (MMA-$d_8$), attenuation values of about 20 dB/km can be realised. In this case, however, an important point is that the perdeuterated monomer, as well as the polymer, must be as pure and as highly deuterated as possible. In fact, it has been found that there is a direct relationship between the degree of deuteration of the polymer and the light attenuation value of the fibre, with the result that the light attenuation is very substantially reduced only when the degree of deuteration is as high as possible.

Thus, it should be possible to synthesise MMA-$d_8$, used as the starting material for the preparation of perdeuterated PMMA, in the most highly deuterated form.

Synthesis processes for perdeuterated methyl methacrylate are known, for example from U.S. Pat. No. 4,138,194. In this process, in accordance with the following equation

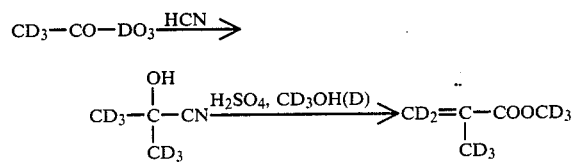

perdeuterated acetone (hexadeuteroacetone, acetone-$d_6$) is first reacted with hydrogen cyanide to give the corresponding cyanohydrin. The latter can then be converted, by treatment with concentrated sulfuric acid and perdeuterated methanol, whereby the cyanohydrin is dehydrated and its nitrile group is hydrolysed and esterified, directly into MMA-$d_8$.

As shown by the applicant's own work and by literature data (Makromol. Chem. 182, 2502 (1981)), however, the degree of deuteration in the ketone part of the resulting MMA-$d_8$ is, with this synthesis route, due to a partial H/D exchange, up to 10% lower than in the acetone-$d_6$ used as the starting material. This loss of deuterium due to H/D exchange can be avoided only if DCN, which, however, is extremely expensive, is used in the cyanohydrin synthesis step in place of HCN.

SUMMARY OF THE INVENTION

It was therefore the object of the invention to discover a synthesis process for MMA-$d_8$, which is economical and in which the loss of deuterium remains as low as possible.

Upon further study of the specification and appended claims, further objects and advantages of this invention will become apparent to those skilled in the art.

It has now been found that perdeuterated methyl methacrylate, in which the degree of deuteration in the ketone part is at most 0.3% lower than in the hexadeuteroacetone used as the starting material, can be obtained when the actone-$d_6$ is reacted with trimethylsilyl cyanide to give 1,3-hexadeutero-2-(trimethylsiloxy)-2-cyano-propane, the trimethylsilyl group is hydrolytically eliminated from this intermediate in the next step and the cyanohydrin produced in this way is converted in a known manner by dehydration, hydrolysis of the nitrile group and esterification into MMA-$d_8$.

The invention therefore relates to a process for the preparation of perdeuterated methacrylates from hexadeuteroactone by conversion into the corresponding cyanohydrin, subsequent elimination of water, hydrolysis of the cyano group and esterification with perdeuterated alkanols, the conversion of hexadeuteroacetone into the cyanohydrin being effected by reaction with trimethylsilyl cyanide to give 1,3-hexadeutero-2-(tri-methylsiloxy)-2-cyano-propane and subsequent hydrolytic elimination of the trimethylsilyl group.

The invention also relates to the use of perdeuterated methacrylates, prepared by a process characterised as above, as a monomer in the preparation of optical fibres based on perdeuterated polymethacrylates.

Moreover, the invention relates to 1,3-hexadeutero-2-(trimethylsiloxy)-2-cyano-propane as a novel compound.

The invention also relates to a process for the preparation of 1,3-hexadeutero-2-(trimethylsiloxy)-2-cyano-propane by reaction of hexadeuteroacetone with trimethylsilyl cyanide.

Furthermore, the invention relates to the use of 1,3-hexadeutero-2-(trimethylsiloxy)-2-cyano-propane as an intermediate stage of perdeuterated methacrylates.

DETAILED DISCUSSION

The process according to the invention is carried out in such a way that acetone-$d_6$ is initially reacted in a first stage with trimethylsilyl cyanide to give 1,3-hexadeutero-2-(trimethylsiloxy)-2-cyano-propane. As is customary for reactions of trimethylsilyl cyanide with carbonyl compounds, this is carried out with acid catalysis by means of anhydrous Lewis acids.

All conventional Lewis acids are suitable as the acid catalyst, such as, for example, aluminium trichloride, iron trichloride, zinc iodide and boron trifluoride etherate. Zinc iodide here proves to be particularly advantageous. The 1,3-hexadeutero-2-(trimethylsiloxy)-2-cyano-propane obtained in a substantially quantitative yield can be prepared in a pure form by, say, distillation or chromatography. However, it can also be employed in the further synthesis in a crude, unpurified form.

This compound is novel and represents a valuable intermediate in the process according to the invention. As a key substance, it opens here a route to a large number of perdeuterated methacrylates, depending on the alcohol which is employed for the esterification in the further synthesis.

This "silylated" cyanohydrin of acetone-d$_6$, prepared by the process according to the invention, has the particular advantage that the degree of deuteration in its ketone part virtually corresponds to that of the perdeuterated starting acetone or is lower by at most 0.3%. In contrast to the cyanohydrin synthesis with HCN according to the state of the art, wherein about 10% of deuterium is lost due to H/D exchange, no H/D exchange takes place in the process according to the invention. This process has the further advantage that it is here not necessary to work with the extremely toxic hydrogen cyanide and corresponding stringent safety precautions can be omitted.

In the further process for the preparation of perdeuterated methacrylates, a hydrolytic elimination of the trimethylsilyl group from the 1,3-hexadeutero-2-(trimethylsiloxy)-2-cyano-propane takes place first to give the deuterated acetone cyanohydrin. For this purpose, the 1,3-hexadeutero-2-(trimethylsiloxy)-2-cyano-propane obtained in the crude form in the preceding step is simply added to an aqueous solution of an inorganic acid, preferably hydrochloric acid or sulfuric acid. The cyanohydrin can then be isolated in a pure form by extraction with an organic solvent, such as, say, methylene chloride, and, if appropriate, purification by distillation. Those skilled in the art are familiar with the reaction conditions and procedures to be applied in detail in such reactions.

The preparation of the perdeuterated methacrylates from the perdeuterated cyanohydrin thus obtained can then proceed in a manner quite analogous to the processes according to the state of the art. Thus, in a manner known per se, the methacrylonitrile can be obtained by elimination of water by concentrated sulfuric acid, and the subsequent hydrolysis of the cyano group to give the methacrylic acid and the esterification of the latter with a perdeuterated alcohol can take place in two separate steps or in one combined step. The detailed procedures and reaction conditions to be selected here are likewise known to those skilled in the art or can readily be taken from the state of the art. In principle, any alcohol, which can be esterified under acid conditions can be employed in this esterification step, independently of whether they are perdeuterated, partially deuterated or not deuterated. Particularly in view of the use as a monomer for the preparation of perdeuterated polymethacrylates for optical fibres, perdeuterated alkanols, or alkanols which are fully deuterated at least in the alkyl moiety, such as, for example, methanol-d$_3$ or -d$_4$ and ethanol-d$_5$ or -d$_6$, are preferred. Methanol-d$_3$ and methanol-d$_4$ are particularly preferred.

A particularly elegant form of the process according to the invention for the preparation of the perdeuterated methacrylates results when the 1,3-hexadeutero-(2-trimethylsiloxy)-2-cyano-propane is reacted in one step to the perdeuterated methacrylate, without isolation of the further intermediate stages. In this case, the crude "silylated" cyanohydrin obtained according to the first process step is treated with concentrated sulfuric acid, the elimination of the trimethylsilyl group, the dehydration and the hydrolysis of the cyano group taking place in a "one-pot" reaction. When the reaction mixture is then caused to react with the perdeuterated alcohol envisaged for the esterification and the product is worked up in the conventional manner, the desired perdeuterated methacrylate is obtained.

Corresponding to the degree of deuteration of the 1,3-hexadeutero-2-(trimethylsiloxy)-2-cyano-propane functioning as an intermediate, the methacrylates prepared by the above process variants have degrees of deuteration in the ketone part which are at most 0.3% lower than those in the acetone-d$_6$ used as the starting material.

Due to their high degree of deuteration, the perdeuterated methacrylates prepared in this way are very particularly suitable as monomers for the preparation of perdeuterated polymethacrylates. The latter can be prepared from the monomers in a completely conventional way by polymerisation processes with which those skilled in the art are familiar. Optical fibres having particularly low light attenuation can be prepared very advantageously from such perdeuterated polymer materials. Appropriate techniques are known from the state of the art, for example from Int. Wire and Cable Symp. 25, 352 (1977), where perdeuterated polymethyl methacrylate is particularly preferred for the preparation of optical fibres.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

1. Preparation of 1,3-hexadeutero-2-(trimethylsiloxy)-2-cyano-propane 32.0 g of acetone-d$_6$ (degree of deuteration; 99.78%) are added dropwise at room temperature, with stirring, to a suspension of 1.0 g of ZnI$_2$ in 50.0 g of tri-methylsilyl cyanide. To complete the reaction, the mixture is then heated to 70° C. for about one hour. After the solid ZnI$_2$ has been separated off, this gives 78.2 g of crude 1,3-hexadeutero-2-(trimethyl-siloxy)-2-cyano-propane. This is employed in the next stage in a form which is not purified further; a part is distilled for characterisation. Boiling point: 45° C., 12 mm Hg. Mass spectrum: 163 (m+).

2. Preparation of methyl methacrylate-d$_8$ 65.2 g of 1,3-hexadeutero-2-(trimethylsiloxy)-2-cyano-propane are added dropwise, with vigorous stirring, to 96 g of 98% sulfuric acid, to which 0.4 g of copper powder has been added for stabilising the end product, the reaction temperature being maintained at 75°–80° C. by cooling when necessary. To complete the reaction, the mixture is heated to 125° C. for a short time. After the reaction mixture has been cooled again to 80° C., a solution of 58.0 g of methanol-d$_4$ (degree of deuteration 99.60%), 16.0 g of water and 2.0 g of hydroquinone is added dropwise. The mixture is boiled under reflux at 140° C. for eight hours and then subjected to steam distillation. The distillate is extracted with methylene chloride, the organic phase is dried and freed from solvent, and the residue is subjected to fractional distillation; boiling point: 99.6° C.

This gives 27.2 g of methyl methacrylate-d$_8$ with a degree of deuteration of 99.60%, determined by NMR spectroscopy against an external standard.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a perdeuterated methacrylate lower alkyl ester which comprises:

(a) reacting hexadeuteroacetone with trimethylsilyl cyanide to form 1,3-hexadeutero-2-(trimethylsiloxy)-2-cyano-propane,
  (b) hydrolyzing said cyanopropane to form hexadeuteroacetone cyanohydrin,
  (c) dehydrating said cyanohydrin to form pentadeuteromethacrylonitrile,
  (d) hydrolyzing said nitrile to form hexadeuteromethacrylic acid, and
  (e) esterifying said acid with a perdeuterated lower alkanol.

2. A process according to claim 1, wherein the perdeuterated lower alkanol is perdeuterated methanol.

* * * * *